(12) United States Patent
Glass (10) Patent No.: US 8,067,191 B2
(45) Date of Patent: Nov. 29, 2011

(54) METHOD FOR DETECTING IL-16 ACTIVITY AND MODULATION OF IL-16 ACTIVITY BASED ON RANTES PROXY PROTEIN LEVELS

(75) Inventor: William G. Glass, Libertyville, IL (US)

(73) Assignee: Centocor, Inc., Malvern, PA (US)

( * ) Notice: Subject to any disclaimer, the term of this patent is extended or adjusted under 35 U.S.C. 154(b) by 249 days.

(21) Appl. No.: 12/304,337

(22) PCT Filed: Jun. 6, 2007

(86) PCT No.: PCT/US2007/070492
§ 371 (c)(1),
(2), (4) Date: Dec. 11, 2008

(87) PCT Pub. No.: WO2007/146702
PCT Pub. Date: Dec. 21, 2007

(65) Prior Publication Data
US 2009/0325188 A1 Dec. 31, 2009

Related U.S. Application Data

(60) Provisional application No. 60/804,468, filed on Jun. 12, 2006.

(51) Int. Cl.
*G01N 33/53* (2006.01)
*A61K 38/16* (2006.01)
*C12N 5/02* (2006.01)

(52) U.S. Cl. ................ 435/7.24; 435/386; 424/85.2

(58) Field of Classification Search ............ None
See application file for complete search history.

(56) References Cited

U.S. PATENT DOCUMENTS

| | | | | |
|---|---|---|---|---|
| 6,936,426 | B2 * | 8/2005 | Smith et al. | 435/7.1 |
| 2006/0106203 | A1 * | 5/2006 | Winter et al. | 530/387.3 |
| 2007/0178605 | A1 * | 8/2007 | Mor et al. | 436/510 |

OTHER PUBLICATIONS

Montes de Oca Arjona et al., Absence of favourable changes in circulating levels of interleukin-16 or β-chemokine concentration following structured intermittent interruption treatment of chronic human immunodeficiency virus infection, Clin. Microbiol. Infect., 11, 57-62, 2005.*
Cheng et al., A549 Cells Can Express Interleukin-16 and Stimulate Eosinophil Chemotaxis, Am. J. Respir., Cell Mol. Biol. 25, 212-218, 2001.*
Cruikshank, et al., "Interleukin-16," Journal of Leukocyte Biology, 67: 757-766 (2000).
Krug, et al., "Interleukin 16 and T-cell Chemoattractant Activity in Bronchoalveolar Lavage 24 Hours after Allergen Challenge in Asthma," American Journal of Respiratory and Critical Care Medicine, 162: 105-111 (2000).
Lard, et al., "Enhanced concentrations of interleukin 16 are associated with joint destruction in patients with rheumatoid arthritis," The Journal of Rheumatology, 31(1): 35-39 (2004).
Mathy, et al., "Cutting Edge: CD4 Is Not Required for the Functional Activity of IL-16," The Journal of Immunology, 164: 4429-4432 (2000).
Reich, et al., "Evidence for a role of Langerhans cell-derived IL-16 in atopic dermatitis," Journal of Allergy and Clinical Immunology, 109: 681-687 (2002).
Ward, et al., "Chemokines and T Lymphocytes: More than an Attraction," Immunity, 9: 1-11 (1998).
Zhang, et al., "Processing and Activation of Pro-Interleukin-16 by Caspase-3," The Journal of Biological Chemistry, 273(2): 1144-1149 (1998).
PCT International Search Report dated Aug. 13, 2008.
Bandeira-Melo, et al., "IL-16 Promotes Leukotrience $C_4$ and IL-4 Release from Human Eosinophils via CD4- and Autocrine CCR3-Chemokine-mediated Signaling," The Journal of Immunology, 168: 4756-4763 (2002).
Pritchard, et al., "Synovial Fibroblasts from Patients with Rheumatoid Arthritis, Like Fibroblasts from Graves' Disease, Express High Levels of IL-16 When Treated with Igs against Insulin-Like Growth Factor-1 Receptor," The Journal of Immunology, 173: 3364-3569 (2004).
Wen, et al., "HIV-1 infection initiates changes in the expression of a wide array of genes in U937 promonocytes and HUT78 T cells," Virus Research, 113: 26-35 (2005).

* cited by examiner

*Primary Examiner* — Elly-Gerald Stoica
(74) *Attorney, Agent, or Firm* — Eric Dichter (57) ABSTRACT

Methods for detecting IL-16 biological activity, detecting modulation of IL-16 biological activity, and diagnosing the presence of or susceptibility of a subject to an IL-16-related disorder involve measuring and comparing the levels of RANTES proxy produced by eukaryotic cells, such as CD4+ and CD9+ cell lines, peripheral blood mononuclear cells, HuT-78 cells, and/or THP-1 cells.

18 Claims, 3 Drawing Sheets

METHOD FOR DETECTING IL-16 ACTIVITY AND MODULATION OF IL-16 ACTIVITY BASED ON RANTES PROXY PROTEIN LEVELS

This application is a §371 application of International Application Number PCT/US2007/070492, filed 6 Jun. 2007, which claims the benefit of U.S. Provisional Application No. 60/804,468, filed 12 Jun. 2006. The entire contents of each of the aforementioned applications is incorporated herein by reference in its entirety.

FIELD OF THE INVENTION

The present invention relates to a method for detecting IL-16 biological activity and detecting modulation of IL-16 biological activity. Additionally, the present invention is directed to a method of diagnosing the presence of and/or susceptibility to an IL-16-related disorder.

BACKGROUND OF THE INVENTION

Interleukin-16 (IL-16; SEQ ID NO: 3) is a pro-inflammatory cytokine that induces positive chemotaxis of T-lymphocytes, monocytes, eosinophils, and dendritic cells (67 J. Leukocyte Biol. 757 (2000)). IL-16 stimulus also increases IL-1b expression, increases IL-6 expression, and increases IL-15 expression in IL-16 responsive eukaryotic cells (67 J. Leukocyte Biol. 757 (2000)).

IL-16 peptide chain monomers are formed by the caspase-3 mediated proteolytic processing of a larger 14 kDa precursor molecule (273 J. Biol. Chem. 1144 (1998)). IL-16 monomers form tetrameric peptide chain complexes. These tetrameric IL-16 complexes are believed to be the bioactive form of IL-16 (67 J. Leukocyte Biol. 757 (2000)). Eukaryotic cells that produce IL-16 include cells that express CD4 or CD8, such as T-cells, mast cells, eosinophils, dendritic cells epithelial cells, fibroblasts, and cells of the cerebellum (67 J. Leukocyte Biol. 757 (2000)). Eukaryotic cells responsive to IL-16 express the CD4 and CD9 peptide chains, but the response to IL-16 may also be independent of these peptide chains (see e.g. 164 J. Immunol. 4429 (2000)).

IL-16 has been reported to play an important role in such diseases as asthma, atopic dermatitis, and rheumatoid arthritis, among others (see e.g. 162 Am. J. Respir. Crit. Care Med. 105 (2000); 109 J. Allergy Clin. Immunol. 681 (2002); 31 J. Rheumatol. 35 (2004). For example, in human patients IL-16 has been shown to be responsible for attracting asthma inducing cells to the lungs and to play a critical role in triggering asthmatic responses in patients (162 Am. J. Respir. Crit. Care Med. 105 (2000)). Clearly, the ability to detect and identify molecules that activate or inhibit IL-16 is critical to the development of effective treatments for IL-16 mediate diseases.

Thus, a need exists for novel methods for detecting IL-16 biological activity, activators of IL-16 biological activity, and inhibitors of IL-16 biological activity.

SUMMARY OF THE INVENTION

One aspect of the invention is a method of detecting IL-16 biological activity in a sample comprising the steps of providing a first population of eukaryotic cells surrounded by media and responsive to IL-16 biological activity with a first test sample; providing a second population of eukaryotic cells surrounded by media and responsive to IL-16 biological activity with a negative control sample; measuring the amount of a RANTES proxy produced by the first and second populations of eukaryotic cells; and comparing the amount of a RANTES proxy produced by the first and second populations of eukaryotic cells wherein a smaller amount of a RANTES proxy produced by the first population of eukaryotic cells relative to the RANTES proxy level produced by the second population of eukaryotic cells indicates the detection of IL-16 biological activity in the test sample.

Another aspect of the invention is a method of detecting a molecule that increases IL-16 biological activity in a sample comprising the steps of providing a first population of eukaryotic cells surrounded by media and responsive to IL-16 biological activity with a first test sample; providing a second population of eukaryotic cells surrounded by media and responsive to IL-16 biological activity with a positive control sample containing biologically active IL-16; measuring the amount of a RANTES proxy produced by the first and second populations of eukaryotic cells; and comparing the amount of a RANTES proxy produced by the first and second populations of eukaryotic cells whereby a smaller amount of a RANTES proxy produced by the first population of eukaryotic cells relative to the RANTES proxy level produced by the second population of eukaryotic cells indicates the presence of a molecule that increases IL-16 biological activity in the test sample.

A method of detecting a molecule that decreases IL-16 biological activity in a sample comprising the steps of providing a first population of eukaryotic cells surrounded by media and responsive to IL-16 biological activity with a first test sample; providing a second population of eukaryotic cells surrounded by media and responsive to IL-16 biological activity with a positive control sample containing biologically active IL-16; measuring the amount of a RANTES proxy produced by the first and second populations of eukaryotic cells; comparing the amount of a RANTES proxy produced by the first and second populations of eukaryotic cells whereby a larger amount of a RANTES proxy produced by the first population of eukaryotic cells relative to the RANTES proxy level produced by the second population of eukaryotic cells indicates the presence of a molecule that decreases IL-16 biological activity in the test sample.

Another aspect of the present invention is a method of diagnosing the presence of or susceptibility to an IL-16-related disorder in a subject comprising the steps of providing a sample from the subject of eukaryotic cells; measuring the amount of a RANTES proxy produced by the sample of eukaryotic cells; and comparing the amount of a RANTES proxy produced by the sample against a reference standard, i.e., cells from a subject not having or susceptible to an IL-16-related disorder, whereby a larger amount of a RANTES proxy produced by the subject sample relative to the RANTES proxy level produced in the standard indicates the presence of or susceptibility to an IL-16-related disorder.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a cell" is a reference to one or more cells and includes equivalents thereof known to those skilled in the art.

Unless defined otherwise, all technical and scientific terms used herein have the same meaning as commonly understood by one of ordinary skill in the art to which this invention belongs. Although any compositions and methods similar or equivalent to those described herein can be used in the practice or testing of the invention, exemplary compositions and methods are described herein.

The term "antibody" means immunoglobulin or antibody molecules comprising polyclonal antibodies, monoclonal antibodies including murine, human, humanized and chimeric monoclonal antibodies and antibody fragments, portions, or variants. Antibodies are secreted proteins constitutively expressed and secreted by plasma cells. Antibodies can also be produced using plasma cells immortalized by standard methods such as hybridoma generation or by transfection of antibody heavy and/or light chain genes into an immortalized B cell such as a myeloma cell or other cell types, such as Chinese hamster ovary (CHO) cells, plant cells and insect cells.

The term "biological activity" means the response of a biological system to a molecule. Such biological systems may be, for example, a cell, a replicable nucleic acid, such as a virus or plasmid, the isolated components of a cell or replicable nucleic acid, or an in vitro system incorporating one or more of these.

The term "CD4" means a peptide chain with at least 50% identity to residues 1 to 433 of SEQ ID NO: 1 and that is responsive to IL-16. Identity between two peptide chains can be determined by pair-wise amino acid sequence alignment using the default settings of the AlignX module of Vector NTI v.9.0.0 (Invitrogen Corp., Carslbad, Calif.). AlignX uses the CLUSTALW algorithm to perform pair-wise amino acid sequence alignments. "CD4" is an acryonym for "Cluster of Determinant antigen 4."

The term "CD9" means a peptide chain with at least 90% identity to residues 1 to 228 of SEQ ID NO: 2 and that is responsive to IL-16. "CD9" is an acryonym for "Cluster of Determinant antigen 9."

The term "eukaryotic cell" means a cell in which genetic material is organized into at least one membrane-bound nucleus.

The term "express" means the detectable production of a peptide chain encoded by a nucleic acid.

The term "IL-16" means a peptide chain with at least 80% identity to amino acid residues 1 to 121 of SEQ ID NO: 3 that can bind CD4 and decrease production of a RANTES proxy. "IL-16" is an acronym for "Interleukin 16."

The term "IL-16-related disorder" means an infectious or immune mediated inflammatory disorder, such as tuberculosis, pneumonia, respiratory syncytial virus, asthma, atopic dermatitis, Crohn's disease, inflammatory bowel disease, rheumatoid arthritis, central nervous system related disorders, such as multiple sclerosis, systemic lupus erythematosis, Graves disease, hepatitis C virus, mumps, coxsackie, echovirus, influenza, *E. Coli* infection, listeria, meningitis, Epstein-Barr virus, and diseases and disorders with related mechanisms and/or characterized by up-regulation of IL-16 or increased IL-16 activity.

The term "peptide chain" means a molecule that comprises at least two amino acid residues linked by a peptide bond to form a chain. Large peptide chains of more than 50 amino acids may be referred to as "polypeptides" or "proteins." Small peptide chains of less than 50 amino acids may be referred to as "peptides."

The term "HuT-78 cells" means cells with ATCC® Number: TIB-161™ from the American Type Culture Collection (ATCC), Manassas, Va. or cells derived from these.

The term "THP-1 cells" means cells with ATCC® Number: TIB-202™ from the American Type Culture Collection (ATCC), Manassas, Va. or cells derived from these.

The term "population" means at least two items such as two cells.

The term "RANTES proxy," also referred to as CCL5, means a peptide chain with at least 75% identity to amino acid residues 1 to 68 of SEQ ID NO: 4, a nucleic acid encoding a peptide chain with at least 75% identity to amino acid residues 1 to 68 of SEQ ID NO: 4, a peptide chain expressed by activating the regulatory region of the native gene encoding SEQ ID NO: 4, or a nucleic acid transcribed by activating the regulatory region of the native gene encoding SEQ ID NO: 4. A RANTES proxy can be used as an indicator of RANTES gene activation. Identity between two peptide chains can be determined by pair-wise amino acid sequence alignment using the default settings of the AlignX module of Vector NTI v.9.0.0 (Invitrogen Corp., Carslbad, Calif.). AlignX uses the CLUSTALW algorithm to perform pair-wise amino acid sequence alignments. "RANTES" is an acronym for "regulated upon activation, normal T-cell expressed, and presumably secreted."

The term "responsive" means capable of producing a detectable signal in reaction to a stimulus.

One aspect of the invention is a method of detecting IL-16 biological activity in a sample (which may indicate the presence of or susceptibility to an IL-16-related disorder) comprising the steps of providing a first population of eukaryotic cells surrounded by media and responsive to IL-16 biological activity with a first test sample; providing a second population of eukaryotic cells surrounded by media and responsive to IL-16 biological activity with a negative control sample; measuring the amount of a RANTES proxy produced by the first and second populations of eukaryotic cells; and comparing the amount of a RANTES proxy produced by the first and second populations of eukaryotic cells whereby a smaller amount of a RANTES proxy produced by the first population of eukaryotic cells relative to the RANTES proxy level produced by the second population of eukaryotic cells indicates the detection of IL-16 biological activity in the test sample.

The magnitude of change of RANTES proxy that indicates changes in IL-16 biological activity is that which is statistically significant, e.g., at least about 1.5 fold, for example, 2-fold, 3-fold, and increasing amounts.

Eukaryotic cells useful in the methods of the invention may be adherent or in suspension. These eukaryotic cells may be surrounded by media suitable for cell growth or maintenance that contains serum or is serum free. Eukaryotic cells useful in the methods of the invention are responsive to IL-16. IL-16 responsive cells respond to IL-16 stimulus by chemotaxis toward an IL-16 source, increased IL-1b expression, increased IL-6, increased IL-15 expression, or decreased RANTES production and can be identified on these bases. Cells that are responsive to IL-16 typically express CD4, CD9 or both CD4 and CD9 any may also be identified on this basis. Test samples and negative control samples may comprise a carrier that is compatible with maintaining IL-16 biological activity in a sample and is compatible with the eukaryotic cells used in the methods of the invention. Phosphate buffered saline (PBS) is one example of such a carrier, those skilled in the art will recognize others. Ideally, negative control samples are known to contain no detectable IL-16 biological activity.

RANTES proxy production may be measured in a variety of different ways. For example, where the RANTES proxy is a peptide chain, production can be measured by RANTES proxy expression assays that specifically detect RANTES proxy peptide chains. Such assays may include SDS-PAGE, Western blotting, ELISA, RANTES proxy specific enzyme assays such as luciferase assays, or RANTES proxy specific antibody conjugated bead analyses. Such RANTES proxy peptide chains may be the RANTES peptide chain of SEQ ID NO: 4 or a peptide chain encoded by a nucleic acid sequence under the control of the regulatory region of the native gene encoding SEQ ID NO: 4. The peptide chain encoded by a nucleic acid sequence under the control of the regulatory region of the native gene encoding SEQ ID NO: 4 may be an easily detected peptide such as, for example, luciferase or green fluorescent protein. Those skilled in the art will recognize other easily detected peptide chains suitable for use in the methods of the invention. Alternatively, where the RANTES proxy is an RNA its production can be measured by RT-PCR, Northern blotting, or other techniques well known by those skilled in the art for detecting specific RNA transcripts.

A nucleic acid sequence may be placed under the control of the regulatory region of the native gene encoding SEQ ID NO: 4 by operably linking this regulatory region to the nucleic acid sequence. Such an operable linkage may be created in the context of an extra-chromosomal nucleic acid, such as a plasmid, that can be used as an extra-chromosomal reporter construct encoding a peptide chain or RNA. Such extra-chromosomal constructs may also be introduced into the chromosomal DNA by random recombination events using transfection techniques well known in the art. Alternatively, such operable linkages may be created in the context of a chromosomal nucleic acid such as chromosomal DNA. The native gene encoding SEQ ID NO: 4 is one example of an operable linkage in the context of a chromosomal nucleic acid. However, as those skilled in the art will recognize, site-specific recombination techniques can be used to operably link a heterologous gene to the regulatory region of a native gene present in chromosomal DNA. The resulting peptide chain or RNA encoded by such a chromosomal nucleic acid can then function as a RANTES proxy.

In one embodiment of the method the eukaryotic cells express a CD4 peptide chain or CD9 peptide chain. CD4 or CD9 peptide chains may be constitutively or inducibly expressed and may be encoded by native genes or heterologous nucleic acids such as cDNAs. Such cDNAs may, for example, encode the peptide chain of SEQ ID NO: 1 or SEQ ID NO: 2.

In another embodiment of the method the eukaryotic cells are selected from the group consisting of peripheral blood mononuclear cells, HuT-78 cells, and THP-1 cells. These eukaryotic cells may be surrounded by media suitable for cell growth or maintenance that contains serum or is serum free.

In another embodiment of the method providing the first test sample produces a final IL-16 concentration in the media surrounding the first population of eukaryotic cells that is 100 ng/ml to 1000 ng/ml. The IL-16 assay methods described here are capable of detecting IL-16 biological activity present in the media surrounding the eukaryotic cells at a concentration of at least 100 ng/ml to 1000 ng/ml IL-16. However, the methods of the invention are also suitable for detecting higher and lower final concentrations of IL-16 in a sample that are outside this range.

In another embodiment of the method the RANTES proxy is secreted into the media. The peptide chain comprising the amino acid sequence of SEQ ID NO: 4 is an example of a RANTES proxy that is secreted into the media. Such RANTES proxies may also be generated by expressing a fusion peptide chain comprising a secretory signal sequence fused to a RANTES proxy peptide chain. One such secretory signal sequence is the Human Growth Hormone (HGH) secretory signal sequence (SEQ ID NO: 5). Those skilled in the art will recognize other appropriate secretory signal sequences.

Another aspect of the invention is a method of detecting a molecule that increases IL-16 biological activity in a sample comprising the steps of providing a first population of eukaryotic cells surrounded by media and responsive to IL-16 biological activity with a first test sample; providing a second population of eukaryotic cells surrounded by media and responsive to IL-16 biological activity with a positive control sample containing biologically active IL-16; measuring the amount of a RANTES proxy produced by the first and second populations of eukaryotic cells; comparing the amount of a RANTES proxy produced by the first and second populations of eukaryotic cells whereby a smaller amount of a RANTES proxy produced by the first population of eukaryotic cells relative to the RANTES proxy level produced by the second population of eukaryotic cells indicates the presence of a molecule that increases IL-16 biological activity in the test sample. This method of invention may be used to detect or identify molecules such as drugs that activate IL-16 biological activity. Such molecules may activate IL-16 biological activity by any mechanism.

Positive control samples may comprise a carrier that is compatible with maintaining IL-16 biological activity in a sample and is compatible with the eukaryotic cells used in the methods of the invention. Phosphate buffered saline (PBS) is one example of such a carrier, those skilled in the art will recognize others. Positive control samples are known to contain detectable IL-16 biological activity.

In one embodiment of the method the eukaryotic cells express a CD4 peptide chain or CD9 peptide chain.

In another embodiment of the method the eukaryotic cells are selected from the group consisting of peripheral blood mononuclear cells, HuT-78 cells, and THP-1 cells.

In another embodiment of the method the first test sample comprises an antibody molecule.

In another embodiment of the method the RANTES proxy is secreted into the media.

Another aspect of the invention is a method of detecting a molecule that decreases IL-16 biological activity in a sample comprising the steps of providing a first population of eukaryotic cells surrounded by media and responsive to IL-16 biological activity with a first test sample; providing a second population of eukaryotic cells surrounded by media and responsive to IL-16 biological activity with a positive control sample containing biologically active IL-16; measuring the amount of a RANTES proxy produced by the first and second populations of eukaryotic cells; comparing the amount of a RANTES proxy produced by the first and second populations of eukaryotic cells whereby a larger amount of a RANTES proxy produced by the first population of eukaryotic cells relative to the RANTES proxy level produced by the second population of eukaryotic cells indicates the presence of a molecule that decreases IL-16 biological activity in the test sample. This method of invention may be used to detect or identify molecules such as drugs that inhibit IL-16 biological activity. Such molecules may inhibit IL-16 biological activity by any mechanism.

The present invention is further described with reference to the following examples. These examples are merely to illustrate aspects of the present invention and are not intended as limitations of this invention.

Example 1

Figure 1:
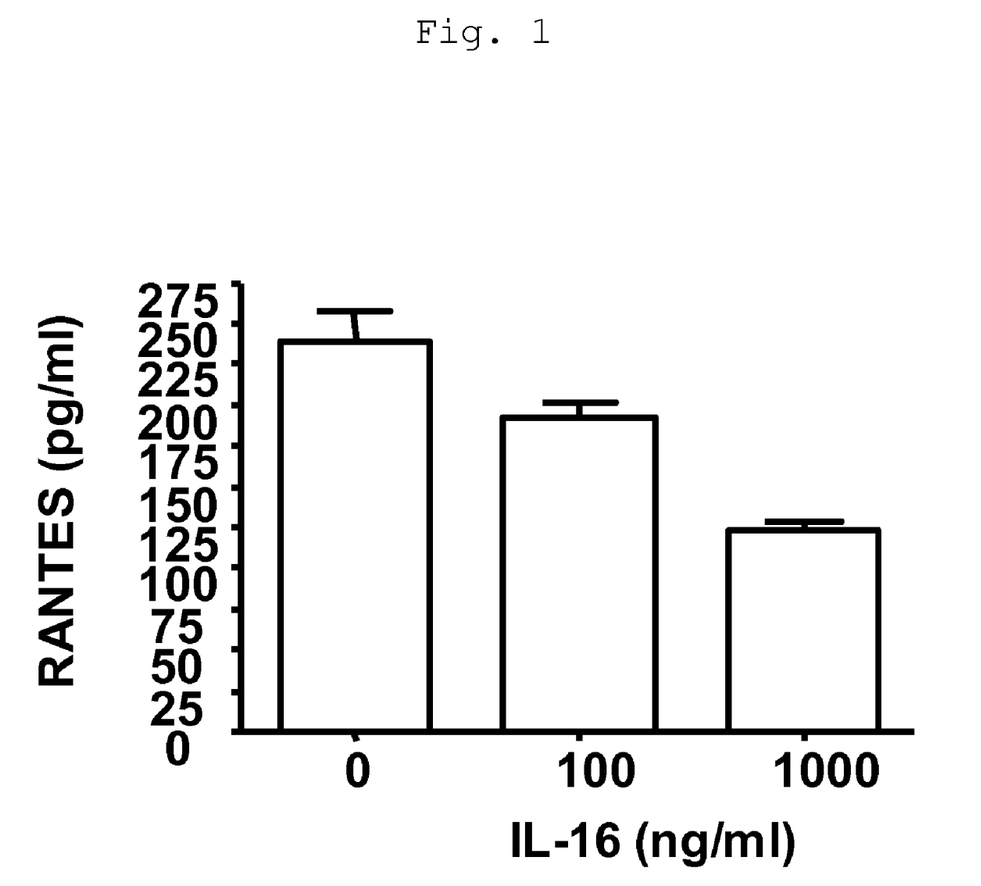
FIG. 1 is a graph showing that IL-16 biological activity decreases RANTES cytokine secretion by peripheral blood mononuclear cells (PBMCs) relative to controls.
Figure 2:
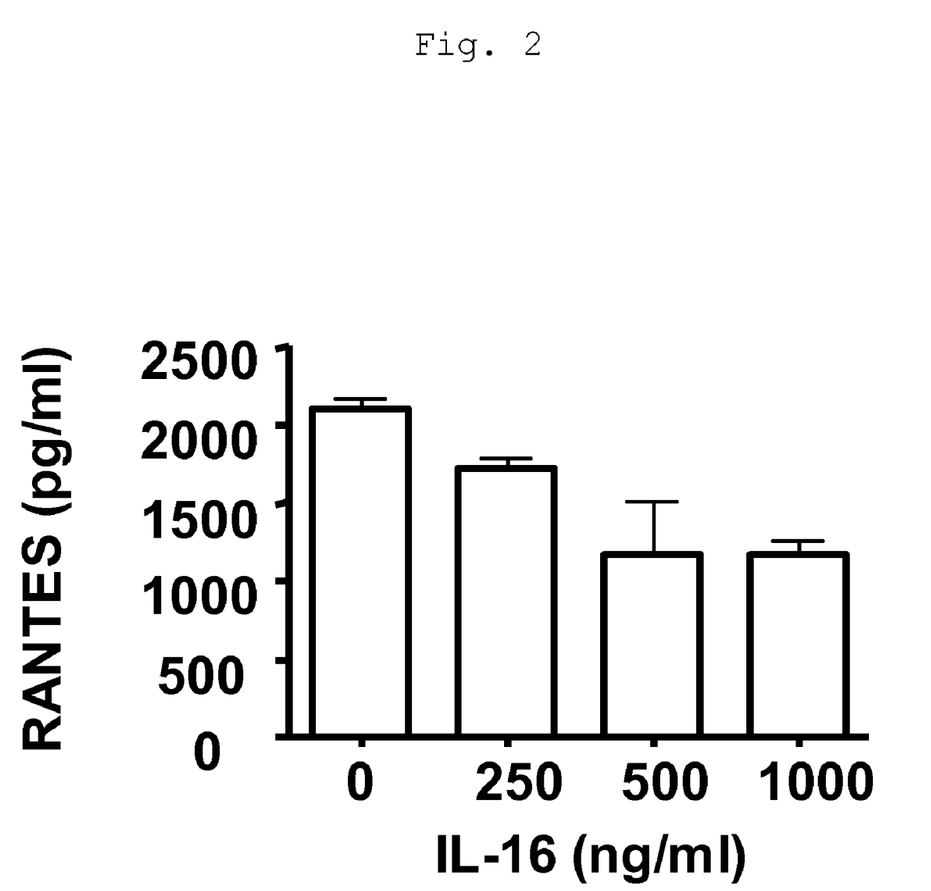
FIG. 2 is a graph showing that IL-16 biological activity decreases RANTES cytokine secretion by HuT-78 cells relative to controls.

Assay Method for Detecting IL-16 Activity and Positive or Negative Modulation of IL-16 Activity Based on Decreased RANTES Levels The presence of IL-16 biological activity in a test sample decreases the level of the RANTES chemotactic cytokine secreted by IL-16 responsive peripheral blood mononuclear cells (PBMCs) or eukaryotic cell lines relative to negative control cells unexposed to a sample containing biologically active IL-16 (FIGS. 1 and 2). Detection of decreased levels of RANTES cytokine secretion by PBMCs (FIG. 1) or IL-16 responsive eukaryotic HuT-78 cells (FIG. 2) receiving a test sample containing unknown molecules can be used to assay for the presence of biologically active IL-16 in the test sample. This assay method can also be used to detect increased or decreased IL-16 biological activity in two different test samples (FIGS. 1 and 2).

Human PBMCs were isolated and maintained in serum free AIM-V® cell culture media (Invitrogen Inc., Carlsbad, Calif.) using standard methods (see e.g. 74 (4) Blood. 1348 (1989)). Immortalized eukaryotic HuT-78 human lymphoblast cells (ATCC® Number: TIB-161™; American Type Culture Collection (ATCC), Manassas, Va.) expressing CD4 (Cluster of Determinant antigen 4) and responsive to IL-16 activity were maintained using standard eukaryotic cell culture techniques in Dulbecco's Modified Eagle Media (D-MEM; Invitrogen Inc., Carlsbad, Calif.) cell culture media containing 20% v/v Fetal Bovine Serum (FBS; Invitrogen Inc., Carlsbad, Calif.).

IL-16 biological activity in test samples was assayed using either isolated PBMC (FIG. 1) or HuT-78 cells (FIG. 2). First, approximately 500,000 PBMC or HuT-78 cells were placed in the wells of a 96 well tissue culture plate containing cell culture media (AIM-V or D-MEM) appropriate for either PBMC (FIG. 1) or HuT-78 cell (FIG. 2) maintenance. Second, a test sample containing biologically active, recombinant Homo sapiens IL-16 (Invitrogen Corp., Carlsbad, Calif.) in phosphate buffered saline (PBS) vehicle was added to each tissue culture well such that the final concentration of biologically active IL-16 in the media surrounding the cells was between 100 ng/ml and 1000 ng/ml (FIG. 1 and FIG. 2). Negative control PBMC or negative control HuT-78 cells did not have test samples containing IL-16 added to the culture wells and instead negative control samples containing PBS vehicle alone were added to the media surrounding these cells (FIGS. 1 and 2). Third, cells receiving test samples containing biologically active IL-16 and negative control cells were then separately incubated for 6 hours at 37° C. under standard eukaryotic cell culture conditions. Fourth, secreted RANTES cytokine levels in the media surrounding cells receiving test samples or negative control cells was measured using RANTES specific Luminex® assays as directed by the manufacturer. Fifth, secreted RANTES cytokine levels in the media surrounding cells that received test samples were compared to RANTES cytokine levels in the media surrounding negative control cells. Decreased levels of secreted RANTES in the media surrounding cells receiving test samples relative to negative control cells was indicative of a test sample containing biologically active IL-16 (FIGS. 1 and 2). Last, secreted RANTES cytokine levels in the media surrounding cells receiving a first test sample containing biologically active IL-16 were compared to RANTES cytokine levels in the media surrounding cells that received a second test sample containing a different amount of biologically active IL-16. The test sample containing the highest amount of IL-16 biological activity can be identified by this comparison because this sample contains the lowest level of secreted RANTES in the media surrounding the cells (FIGS. 1 and 2). The test sample containing the lowest amount of IL-16 biological activity can be identified by this comparison because this sample contains the highest level of secreted RANTES in the media surrounding the cells (FIGS. 1 and 2).

These results demonstrate that IL-16 activity in a sample can be detected by a cell based assay method in which RANTES secretion by IL-16 responsive cells exposed to a test sample containing biologically active IL-16 is decreased relative to negative control cells that did not receive the test sample.

These results also demonstrate that the IL-16 biological activity assay described above can be used to identify test samples containing increased or decreased IL-16 activity. Consequently, the assay described above is suitable for the detection or identification of molecules that increase or decrease IL-16 activity in a sample. Such molecules may be drugs that increase IL-16 activity or simply be additional molecules of biologically active IL-16 that have been added to a sample. Alternatively, such molecules may be drugs that decrease IL-16 activity. Consequently, the assay describe here can detect positive or negative modulation of IL-16 activity in a test sample and can be used to detect or identify molecules, such as drugs, that modulate IL-16 biological activity.

Asterisks indicate statistically significant difference relative to negative controls at a $P<0.05$ using the Student's T-Test (FIGS. 1 and 2).

Example 2

Figure 3:
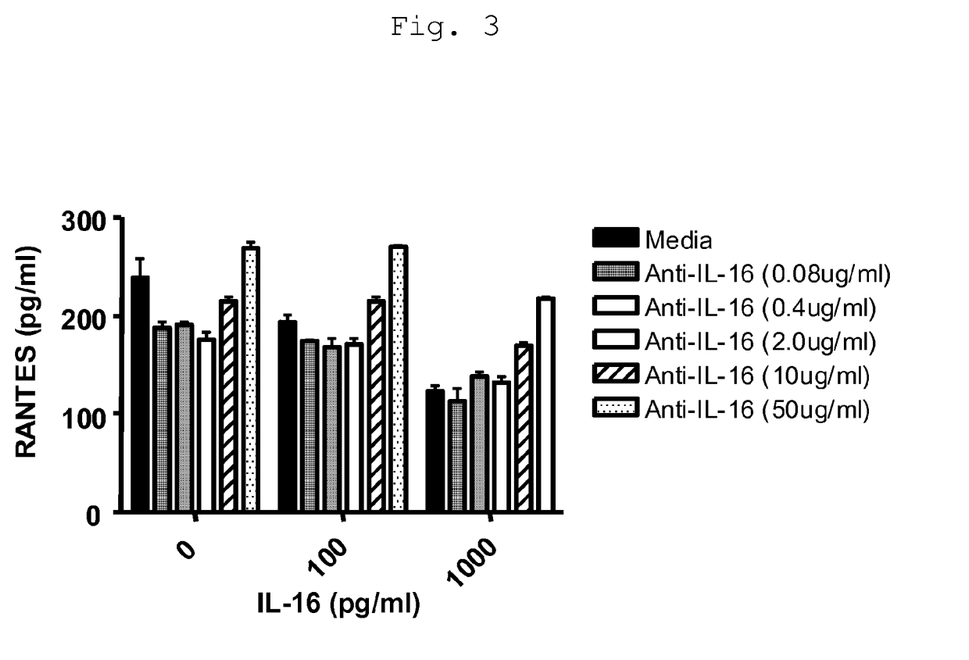
FIG. 3 is a graph showing that inhibitors of IL-16 biological activity increase RANTES cytokine secretion by PMBCs relative to controls.

Assay Method for Detecting Molecules that Modulate IL-16 Activity Based on Decreased RANTES Levels The assay method described in Example 1 above may be modified to permit the detection or identification of molecules (e.g., drugs) in a test sample that modulate IL-16 activity. Such molecules may be, for example, inhibitors of IL-16 activity. As shown in FIG. 3, RANTES cytokine secretion by PBMCs receiving a test sample that contains an inhibitor of IL-16 biological activity is increased relative to positive control cells receiving a test sample containing IL-16 alone. Consequently, the modified assay method described here can be used to detect or identify molecules that modulate IL-16 biological activity.

Assays methods for detecting or identifying molecules that modulate IL-16 activity are performed as follows. First, approximately 500,000 PBMC cells were placed in the wells of a 96 well tissue culture plate containing AIM-V cell culture media. PBMC cells were obtained and maintained as described in Example 1 above. Second, a test sample containing biologically active, recombinant Homo sapiens IL-16 (Invitrogen Corp., Carlsbad, Calif.) in phosphate buffered saline (PBS) vehicle and an antibody that inhibits IL-16 biological activity in vitro was added to each tissue culture well.

As indicated in FIG. 3, IL-16 was added such that the final concentration of biologically active IL-16 in the media surrounding the cells was either 100 ng/ml or 1000 ng/ml. The anti-human IL-16 antibody was a murine, monoclonal antibody that inhibits IL-16 biological activity. Negative control PBMC cells did not have IL-16 added to the culture wells and instead negative control samples containing PBS vehicle alone or the inhibitory anti-IL-16 mAb were added at the concentrations indicated in FIG. 3 to the media surrounding these cells. Positive control PBMC cells received biologically active IL-16 alone such that the final concentration of biologically active IL-16 in the media surrounding cells was either 100 ng/ml or 1000 ng/ml as indicated in FIG. 3. Third, PBMC cells receiving test samples, negative control PBMC cells, and positive control PBMC cells were then separately incubated for 6 hours at 37° C. under standard eukaryotic cell culture conditions. Fourth, secreted RANTES cytokine levels in the media surrounding cells receiving test samples, negative control cells, or positive control cells was measured using RANTES specific Luminex® assays as directed by the manufacturer. Fifth, secreted RANTES cytokine levels in the media surrounding cells that received test samples containing biologically active IL-16 and the inhibitory anti-IL-16 mAb were compared to RANTES cytokine levels in the media surrounding positive control cells receiving biologically active IL-16 alone. Increased levels of secreted RANTES in the media surrounding cells receiving test samples relative to positive control cells was indicative of a test sample containing an inhibitor of biologically active IL-16 (FIG. 3).

These results demonstrate that the IL-16 biological activity assay described above can be used to detect or identify molecules that modulate IL-16 activity in a test sample. Such molecules may be drugs that inhibit IL-16 activity or alternatively drugs that increase IL-16 activity.

Error bars represent the standard deviation from the mean (FIG. 3).

The present invention now being fully described, it will be apparent to one of ordinary skill in the art that many changes and modifications can be made thereto without departing from the spirit or scope of the appended claims.

The invention claimed is:

1. A method of detecting IL-16 biological activity in a sample comprising the steps of:
   a) providing a first population of eukaryotic cells surrounded by media and responsive to IL-16 biological activity with a first test sample;
   b) providing a second population, of the same type of eukaryotic cells as in a) and surrounded by media and responsive to IL-16 biological activity, with a negative control sample;
   c) measuring the amount of a RANTES proxy protein produced by the first and second populations of eukaryotic cells; and
   d) comparing the amount of a RANTES proxy protein produced by the first and second populations of eukaryotic cells, wherein a smaller amount of a RANTES proxy protein produced by the first population of eukaryotic cells relative to the RANTES proxy protein level produced by the second population of eukaryotic cells indicates the detection of IL-16 biological activity in the test sample.

2. The method of claim 1 wherein the eukaryotic cells express a CD4 peptide chain or CD9 peptide chain.

3. The method of claim 2 wherein the eukaryotic cells are selected from the group consisting of peripheral blood mononuclear cells, HuT-78 cells, and THP-1 cells.

4. The method of claim 1 wherein providing the first test sample produces a final IL-16 concentration in the media surrounding the first population of eukaryotic cells that is 100 ng/ml to 1000 ng/ml.

5. The method of claim 1 wherein the RANTES proxy protein is secreted into the media.

6. The method of claim 1, wherein the smaller amount of RANTES proxy protein produced by the first population relative to the second population is at least about a 1.5 fold decrease.

7. A method of detecting a molecule that increases IL-16 biological activity in a sample comprising the steps of:
   a) providing a first population of eukaryotic cells surrounded by media and responsive to IL-16 biological activity with a first test sample;
   b) providing a second population, of the same type of eukaryotic cells as in a) and surrounded by media and responsive to IL-16 biological activity, with a positive control sample containing biologically active IL-16;
   c) measuring the amount of a RANTES proxy protein produced by the first and second populations of eukaryotic cells; and
   d) comparing the amount of a RANTES proxy protein produced by the first and second populations of eukaryotic cells, wherein a smaller amount of a RANTES proxy protein produced by the first population of eukaryotic cells relative to the RANTES proxy protein level produced by the second population of eukaryotic cells indicates the presence of a molecule that increases IL-16 biological activity in the test sample.

8. The method of claim 7 wherein the eukaryotic cells express a CD4 peptide chain or CD9 peptide chain.

9. The method of claim 8 wherein the eukaryotic cells are selected from the group consisting of peripheral blood mononuclear cells, HuT-78 cells, and THP-1 cells.

10. The method of claim 7 wherein the first test sample comprises an antibody molecule.

11. The method of claim 7 wherein the RANTES proxy protein is secreted into the media.

12. The method of claim 7, wherein the smaller amount of RANTES proxy protein produced by the first population relative to the second population is at least about a 1.5 fold decrease.

13. A method of detecting a molecule that decreases IL-16 biological activity in a sample comprising the steps of:
   a) providing a first population of eukaryotic cells surrounded by media and responsive to IL-16 biological activity with a first test sample;
   b) providing a second population, of the same type of eukaryotic cells as in a) and surrounded by media and responsive to IL-16 biological activity, with a positive control sample containing biologically active IL-16;
   c) measuring the amount of a RANTES proxy protein produced by the first and second populations of eukaryotic cells; and
   d) comparing the amount of a RANTES proxy protein produced by the first and second populations of eukaryotic cells, wherein a larger amount of a RANTES proxy protein produced by the first population of eukaryotic cells relative to the RANTES proxy protein level produced by the second population of eukaryotic cells indicates the presence of a molecule that decreases IL-16 biological activity in the test sample.

14. The method of claim 13 wherein the eukaryotic cells express a CD4 peptide chain or CD9 peptide chain.

15. The method of claim 14 wherein the eukaryotic cells are selected from the group consisting of peripheral blood mononuclear cells, HuT-78 cells, and THP-1 cells.

16. The method of claim 13 wherein the first test sample comprises an antibody molecule.

17. The method of claim 13 wherein the RANTES proxy protein is secreted into the media.

18. The method of claim 13, wherein the larger amount of RANTES proxy protein produced by the first population relative to the second population is at least about a 1.5 fold increase.

* * * * *

SEQUENCE LISTING

```
<160> NUMBER OF SEQ ID NOS: 5

<210> SEQ ID NO 1
<211> LENGTH: 433
<212> TYPE: PRT
<213> ORGANISM: Homo sapiens

<400> SEQUENCE: 1

Lys Lys Val Val Leu Gly Lys Lys Gly Asp Thr Val Glu Leu Thr Cys
  1               5                  10                  15

Thr Ala Ser Gln Lys Lys Ser Ile Gln Phe His Trp Lys Asn Ser Asn
             20                  25                  30

Gln Ile Lys Ile Leu Gly Asn Gln Gly Ser Phe Leu Thr Lys Gly Pro
         35                  40                  45

Ser Lys Leu Asn Asp Arg Ala Asp Ser Arg Arg Ser Leu Trp Asp Gln
     50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Glu Val Gln Leu Leu
                 85                  90                  95

Val Phe Gly Leu Thr Ala Asn Ser Asp Thr His Leu Leu Gln Gly Gln
                100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
        130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
        195                 200                 205

Gly Ser Gly Glu Leu Trp Trp Gln Ala Glu Arg Ala Ser Ser Ser Lys
    210                 215                 220
```

```
Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
            245                 250                 255

Leu Thr Leu Pro Gln Ala Leu Pro Gln Tyr Ala Gly Ser Gly Asn Leu
        260                 265                 270

Thr Leu Ala Leu Glu Ala Lys Thr Gly Lys Leu His Gln Glu Val Asn
    275                 280                 285

Leu Val Val Met Arg Ala Thr Gln Leu Gln Lys Asn Leu Thr Cys Glu
290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
            325                 330                 335

Asn Pro Glu Ala Gly Met Trp Gln Cys Leu Leu Ser Asp Ser Gly Gln
        340                 345                 350

Val Leu Leu Glu Ser Asn Ile Lys Val Leu Pro Thr Trp Ser Thr Pro
    355                 360                 365

Val Gln Pro Met Ala Leu Ile Val Leu Gly Gly Val Ala Gly Leu Leu
370                 375                 380

Leu Phe Ile Gly Leu Gly Ile Phe Phe Cys Val Arg Cys Arg His Arg
385                 390                 395                 400

Arg Arg Gln Ala Glu Arg Met Ser Gln Ile Lys Arg Leu Leu Ser Glu
            405                 410                 415

Lys Lys Thr Cys Gln Cys Pro His Arg Phe Gln Lys Thr Cys Ser Pro
        420                 425                 430

Ile

<210> SEQ ID NO 2
<211> LENGTH: 228
<212> TYPE: PRT
<213> ORGANISM: Homo sapiens

<400> SEQUENCE: 2

Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
            85                  90                  95

Leu Val Ile Phe Ala Ile Glu Ile Ala Ala Ala Ile Trp Gly Tyr Ser
        100                 105                 110

His Lys Asp Glu Val Ile Lys Glu Val Gln Glu Phe Tyr Lys Asp Thr
    115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
```

```
                    165                 170                 175

Thr Val Lys Ser Cys Pro Asp Ala Ile Lys Glu Val Phe Asp Asn Lys
                180                 185                 190

Phe His Ile Ile Gly Ala Val Gly Ile Gly Ile Ala Val Val Met Ile
            195                 200                 205

Phe Gly Met Ile Phe Ser Met Ile Leu Cys Cys Ala Ile Arg Arg Asn
        210                 215                 220

Arg Glu Met Val
225

<210> SEQ ID NO 3
<211> LENGTH: 121
<212> TYPE: PRT
<213> ORGANISM: Homo sapiens

<400> SEQUENCE: 3

Ser Ala Ala Ser Ala Ser Ala Ala Ser Asp Val Ser Val Glu Ser Thr
 1               5                  10                  15

Ala Glu Ala Thr Val Cys Thr Val Thr Leu Glu Lys Met Ser Ala Gly
                20                  25                  30

Leu Gly Phe Ser Leu Glu Gly Gly Lys Gly Ser Leu His Gly Asp Lys
            35                  40                  45

Pro Leu Thr Ile Asn Arg Ile Phe Lys Gly Ala Ala Ser Glu Gln Ser
        50                  55                  60

Glu Thr Val Gln Pro Gly Asp Glu Ile Leu Gln Leu Gly Gly Thr Ala
65                  70                  75                  80

Met Gln Gly Leu Thr Arg Phe Glu Ala Trp Asn Ile Ile Lys Ala Leu
                85                  90                  95

Pro Asp Gly Pro Val Thr Ile Val Ile Arg Arg Lys Ser Leu Gln Ser
            100                 105                 110

Lys Glu Thr Thr Ala Ala Gly Asp Ser
        115                 120

<210> SEQ ID NO 4
<211> LENGTH: 68
<212> TYPE: PRT
<213> ORGANISM: Homo sapiens

<400> SEQUENCE: 4

Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Met Ser
65

<210> SEQ ID NO 5
<211> LENGTH: 26
<212> TYPE: PRT
<213> ORGANISM: Homo sapiens
```

-continued

<400> SEQUENCE: 5

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25